United States Patent [19]

Turner et al.

[11] Patent Number: 5,106,631
[45] Date of Patent: Apr. 21, 1992

[54] CHEESE PRODUCTION

[75] Inventors: Jeffrey D. Turner, Coteau-du-Lac; Ioannis Politis, Guelph; Elliott Block, Ste-Anne de Bellevue, all of Canada

[73] Assignee: American Cyanamid Company, Stamford, Conn.

[21] Appl. No.: 380,962

[22] Filed: Jul. 17, 1989

[51] Int. Cl.$^5$ .............................................. A23C 19/00
[52] U.S. Cl. ........................................ 426/2; 514/21; 426/582
[58] Field of Search .................. 514/21; 426/582, 2

[56] References Cited

PUBLICATIONS

Akers J. Dairy Sci 68:501–519 (1985).
Baer et al. J. Dairy Sci 72:1424–1434 (1989).
Bauman et al. J. Dairy Sci 68:1352–1362 (1985).
Cotes et al. Nature vol. 164:992–993 (1949).
Collier et al. J. Dairy Sci 71 (Suppl. 1):228 (1988).
DeJong Neth. Milk Dairy J. 30:242–253 (1976).
Disenhaus et al. Reprod. Nutr. Develop. 28:241–252 (1988).
Donnelly et al. J. Dairy Sci 50:433–441 (1983).
Elvinger et al. J. Dairy Sci 71:1515–1525 (1988).
Eppand et al. J. Dairy Sci 68:3047–3054.
Gertler et al. Mol. Cell. Endocri 33:169–182 (1983).
Hart et al. Life Sciences 27:1839–1847 (1980).
Holst et al. J. Dairy Sci 70:935–944 (1987).
Koryoka-Dahl et al. J. Dairy Sci 66: 704–711 (1983).
Larsson et al. J. of Cell Biol. vol. 98:894–903 (1984).
Ossowski et al. Cell vol. 16 pp. 929–940 (1979).
Pearse et al. J. Dairy Res. 53:477–480 (1986).
Politis et al. J. Dairy Sci 72:900 (1988).
Richard et al. J. Dairy Sci 68:2385–2389 (1985).
Richardson N Z J. Dairy Sci & Tech. 18:247–252 (1983).
Soderholn et al. J. Dairy Sci 71:355–365.
Turner et al. Am J. Physiol. 255; E 513.
Walstra et al. Dairy Chem. & Physics p. 132.
Grufferty et al. J. of Dairy Research (1988) vol. 55(4) 609–630.
Tyrrell et al. J. Nutr. 118:1024–1030.

Primary Examiner—Howard E. Schain
Assistant Examiner—Choon P. Koh
Attorney, Agent, or Firm—Estelle J. Tsevdos

[57] ABSTRACT

The present invention relates to methods for improving cheese production by utilizing plasmin-regulating agents to maintain milk plasmin concentration in milk used to make cheese at that found at early lactation or at less than 0.2 mg/l milk.

4 Claims, 3 Drawing Sheets

CHEESE PRODUCTION

BACKGROUND OF THE INVENTION

The present invention relates to methods for improving cheese production by utilizing plasmin-regulating agents to maintain plasmin in the animal's milk at levels less than 0.2 mg/l milk. All animals whose milk is used to produce cheese benefit from the administration of the plasmin-affecting agents of the present invention. For instance, milk from cows, sheep, goats or even buffalo, to name a few, is used in cheese production. One such compound is bovine somatotropin (hereinafter referred to as BST).

Plasmin is a component of an animal's blood and appears to be involved with fibrinolysis primarily. However, plasmin also has been implicated in cell migration and differentiation, involution of the uterus and mammary gland. Often times, plasminogen activator is synthesized by the target tissue in order to generate localized plasmin production.

Plasmin interacts with milk and cheese in a very particular manner. It seems that milk plasmin increases in late lactation resulting in the increased formation of gamma caseins from the proteolysis of alpha-s and beta casein (Donnelly, 1983). Observed at the same time is an increase in plasminogen activator during natural mammary gland involution or during hormonally induced involution in cell culture. Such an increase in plasminogen activators may be speculated to increase plasmin concentrations with a subsequent degradation of milk proteins.

Recently, an increase in bovine milk plasmin has been observed in late lactation. Further, bovine milk also fluctuates in milk plasmin concentrations depending on the season of the year. Generally, in the spring plasmin and plasminogen are lower, and in the winter plasmin and plasminogen seem to be higher. Additionally, during mastitis or during periods of elevated somatic cell counts, milk plasmin seems to be increased. The decrease in the integrity of the alveslar epithelia within the mammary gland results in an increased transfer of blood plasminogen/plasmin to milk.

Proteolysis of kappa-casein is necessary in cheese production. However, excess non-specific proteolyisis reduces firmness when cheese is being produced. In the more neutral pH cheeses, such as swiss cheese, plasmin is highest, and it is lowest in the acid cheeses such as cheshire cheese. Plasmin degrades beta casein into three components. Also, plasmin has been reported to induce gelation of ultra high temperature pasteurized milk. The formation of amino acids during cheddar cheese ripening yields production of bitter flavors in milk and dairy products and decreasing cheese yield and quality. If milk is incubated with plasmin longer than four hours there is a resulting increase in time necessary to form a rennet clot which is necessary in cheese production.

Difficulties in cheese production from milk exposed to increased levels of plasmin concentration are observed due to seasonal calving in some parts of the world, and therefore, a method to increase cheese production is desireable and will allow cheese manufacture help in such areas of cheese shortages. If milk is processed 1 to 3 days after it is collected from the cow, obviously a high level of plasmin coupled with long incubation time will degrade the alpha-s and beta caseins thereby reducing cheese yield. External modulators which can minimize fluctuation in plasma concentration over lactation or prevent plasmin increases during diseases (mastitis) have tremendous potential in insuring consistent milk for cheese processing and results.

Surprisingly, it has been observed that with injections of recombinant bovine somatotropin (BST), as an example of a plasmin-regulating agent, milk plasmin concentrations observed in late lactations revert to those of early lactation, i.e., the milk plasmin concentration decreases. Thus, a method to improve cheese production yields by administering compounds which decrease milk plasmin levels is provided herein.

SUMMARY OF THE INVENTION

Figure 1:
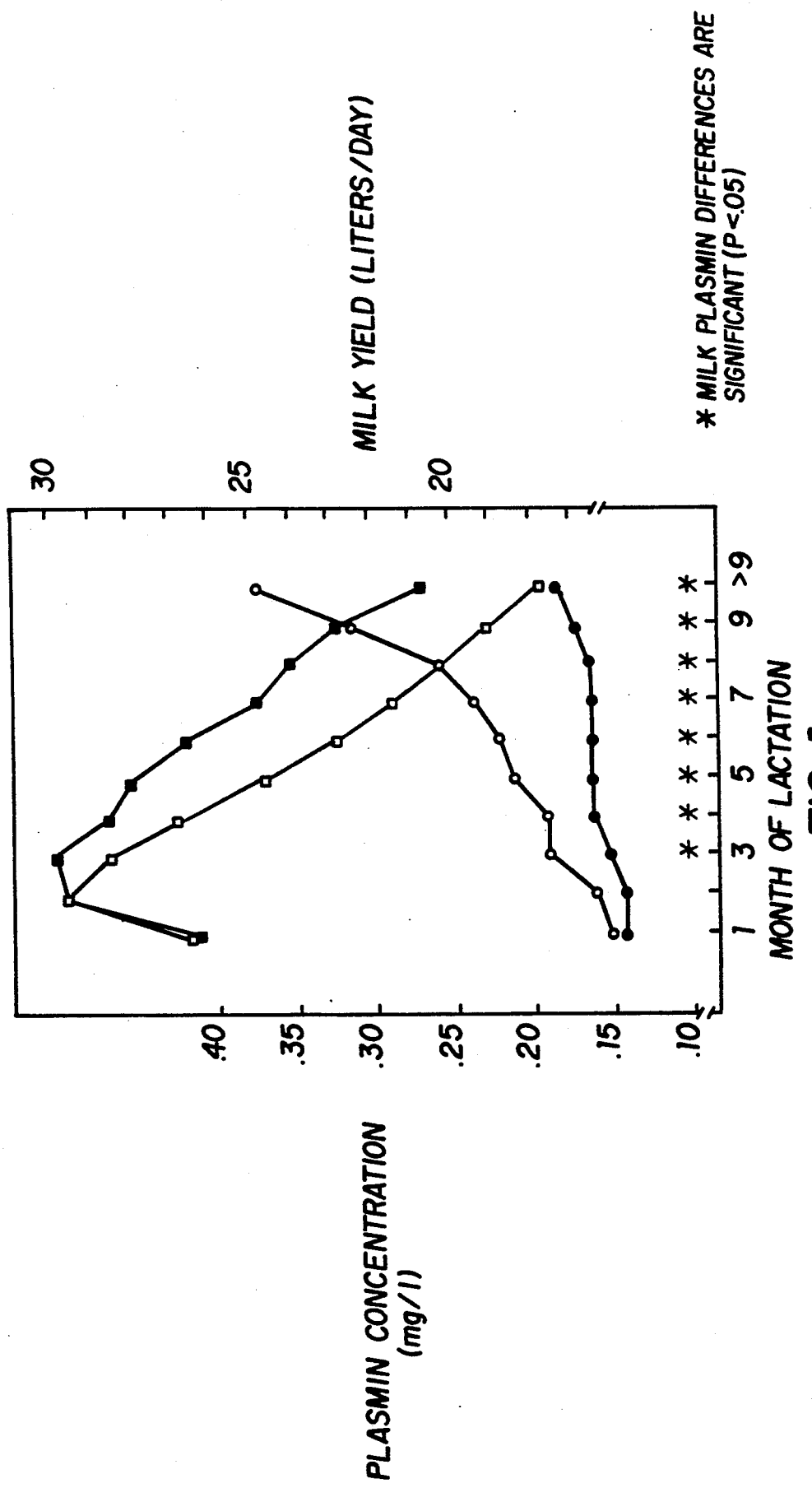
FIG. 1: Relationship between milk plasmin concentration and milk yield in control and rBST-injected cows. Plasmin concentration shown in circles for milk from control (●) or rBST-injected cows (●). Daily milk yield shown in squares for milk from control (□) or rBST-injected cows (■). All values represent least squares means.

The present invention, therefore, provides methods for improving cheese production yields by administering to a milk-producing animal, a plasmin-affecting amount of a plasmin-regulating agent. Specifically, plasmin levels maintained in milk used to produce cheese of less than 0.2 mg/l of milk (0.2 mg/l to 0.001 mg/l) provide the beneficial improvement in cheese production.

The plasmin-regulating agents of the present invention include exogenous animal somatotropins, such as bovine somatotropin, ovine somatotropin, caprine somatotropin, and even buffalo somatotropin. Also, included as another example of a plasmin-regulating agent useful in the present invention is epsilon-amino caproic acid.

It is an object of the present invention, therefore, to provide methods for improving cheese production by administering a plasmin-regulating agent to an animal whose milk is used in cheese production in order to provide milk that is more suitable and increases cheese quality and/or production. Further, it is an object of the present invention to provide methods for increasing cheese production by utilizing milk that has been derived from cows administered such agents. One such agent is recombinantly derived bovine somatotropin (rBST). Another such component is episilon-amino caproic acid. These and further objects of the invention will become obvious by the more detailed description of the invention provided hereinafter.

DETAILED DESCRIPTION OF INVENTION

The following examples are provided as illustrative of the present invention and not limitative thereof.

EXAMPLE 1

Experimental Animals - Efficacy

Seventy-seven Holstein cows are used in the experiments. Forty-two cows are assigned to groups of 14 animals each. Each group is injected with either 10.3 mg animal $^{-1}$ day $^{-1}$ BST subcutaneously, 175 mg or 350 mg BST animal $^{-1}$ 14 days $^{-1}$ in a sustained-release preparation injected subcutaneously. Injections commence at 35 d postpartum for the entire lactation. The remaining 35 cows, serving as controls, receive placebo injections. Cows are fed total mixed rations formulated for National Research Council (1978) requirements for production. Ration ingredients are alfalfa haylage, dry ground corn, high moisture ear corn, roasted soybeans and a vitamin-mineral premix. One thousand two hundred milk samples are collected at two-week intervals from fall into spring. Milk samples are defatted and the skim milk centrifuged at 100,000 $\times$g for 1h at 4° C. to resolve the milk serum fraction from the casein pellet. Daily milk yield is also recorded Injection of BST increases milk yield, and yield of major components in a dose-dependent, linear fashion. This increase is relatively instantaneous, and occurs through an increase in feed intake and improved efficiency of converting feed into milk. Lactation curves generally show improved persistency of production.

EXAMPLE 2

Compositions and Doses of BST

The exogenous animal somatotropins of the present invention are illustrated hereinbelow, but include chemically synthesized, naturally purified from pituitary glands and/or recombinantly-derived.

Recombinantly-derived animal somatotropins without the additional Asp-Gln substitutions or with other substitutions are used in accordance with the present invention, as well. Further, animal somatotropins with deletions in amino acid chain length, additions to amino acid chain length, replacement of amino acids, fragments with the active portion and the like all within the scope of the present invention. Numbering of amino acid residues herein relates to the Met-Asp-Gln analogues, but numbering is altered accordingly by one skilled in the art.

Recombinant Bovine Somatotropin

H—Met—Asp—Gln—Phe—Pro—Ala—Met—Ser—Leu—Ser—

Gly—Leu—Phe—Ala—Asn—Ala—Val—Leu—Arg—Ala—Gln—

His—Leu—His—Gln—Leu—Ala—Ala—Asp—Thr—Phe—Lys—

Glu—Phe—Glu—Arg—Thr—Tyr—Ile—Pro—Glu—Gly—Gln—
55

Arg—Tyr—Ser—Ile—Gln—Asn—Thr—Gln—Val—Ala—Phe—

$R_2$—Phe—Ser—Glu—Thr—Ile—Pro—Ala—Pro—Thr—

Gly—Lys—Asn—Glu—Ala—Gln—Gln—Lys—Ser—Asp—Leu—

Glu—Leu—Leu—Arg—Ile—Ser—Leu—Leu—Leu—Ile—Gln—

Ser—Trp—Leu—Gly—Pro—Leu—Gln—Phe—Leu—Ser—Arg—

-continued

Val—Phe—Thr—Asn—Ser—Leu—Val—Phe—Gly—Thr—Ser—

Asp—Arg—Val—Tyr—Glu—Lys—Leu—Lys—Asp—Leu—Glu—

Glu—Gly—Ile—Leu—Ala—Leu—Met—Arg—Glu—Leu—Glu—

Asp—Gly—Thr—Pro—Arg—Ala—Gly—Gln—Ile—Leu—Lys—

Gln—Thr—Tyr—Asp—Lys—Phe—Asp—Thr—Asn—Met—Arg—

Ser—Asp—Asp—Ala—Leu—Leu—Lys—Asn—Tyr—Gly—
166

Leu—Leu—Ser—$R_{2a}$—Phe—Arg—Lys—Asp—Leu—His—
183

Lys—Thr—Glu—Thr—Tyr—Leu—Arg—Val—Met—Lys—$R_1$—
191

Arg—Arg—Phe—Gly—Glu—Ala—Ser—$R_{1a}$—Ala—Phe—OH.

Recombinant Ovine Somatotropin

H—Met—Asp—Gln—Phe—Pro—Ala—Met—Ser—Leu—Ser—

Gly—Leu—Phe—Ala—Asn—Ala—Val—Leu—Arg—Ala—Gln—

His—Leu—His—Gln—Leu—Ala—Ala—Asp—Thr—Phe—Lys—

Glu—Phe—Glu—Arg—Thr—Tyr—Ile—Pro—Glu—Gly—Gln—
55

Arg—Tyr—Ser—Ile—Gln—Asn—Thr—Gln—Val—Ala—Phe—

$R_2$—Phe—Ser—Glu—Thr—Ile—Pro—Ala—Pro—Thr—Gly—

Lys—Asp—Glu—Ala—Gln—Gln—Lys—Ser—Asp—Leu—Glu—

Leu—Leu—Arg—Ile—Ser—Leu—Leu—Leu—Ile—Gln—Ser—

Trp—Leu—Gly—Pro—Leu—Gln—Phe—Leu—Ser—Arg—Val—

Phe—Thr—Asn—Ser—Leu—Val—Phe—Gly—Thr—Ser—Asp—

Arg—Val—Tyr—Glu—Lys—Leu—Lys—Asp—Leu—Glu—Glu—

Gly—Ile—Leu—Ala—Leu—Met—Arg—Glu—Leu—Glu—Asp—

Val—Thr—Pro—Arg—Ala—Gly—Gln—Ile—Leu—Lys—Gln—

Thr—Tyr—Asp—Lys—Phe—Asp—Thr—Asn—Met—Arg—Ser—

Asp—Asp—Ala—Leu—Leu—Lys—Asn—Tyr—Gly—Leu—
166

Leu—Ser—$R_{2a}$—Phe—Arg—Lys—Asp—Leu—His—Lys—
183

Thr—Glu—Thr—Tyr—Leu—Arg—Val—Met—Lys—$R_1$—
191

Arg—Arg—Phe—Gly—Glu—Ala—Ser—Ala—Phe—OH.

wherein $R_1$, $R_{1a}$, $R_2$ and $R_{2a}$ of said recombinant animal somatotropins each independently represent amino acid residues selected from arginine, lysine, aspartic acid, glutamic acid, asparagine, glutamine, histidine, alanine, glycine, isoleucine, leucine, valine, phenylalanine, tryptophan, tyrosine, methionine, serine, threonine, proline or cystine; additionally $R_1$, $R_{1a}$ or, $R_2$ and $R_{2a}$ in the above illustrated somatotropins, represents an amino acid residue other than cysteine.

Compositions

In practice, the compositions useful in the present invention are generally administered to the animals by injection in the form of biologically active parenteral compositions. Among the parenteral compositions useful for administration of the animal somatotropins of this invention are gels, pastes, microspheres, microcapsules, implants and the like. As such, there is considerable interest in providing dosage forms of biologically active substances which release the substance in a controlled manner and thus, reduce the frequency of administration.

The compositions useful for this type of administration are prepared by dissolving the animal somatotropin in dilute ammonium hydroxide and then adding a solution of an alkali metal benzoate, laurate, carbonate or the like thereto. A nonionic surfactant is thereafter admixed with the solution and the resulting mixture spray dried. The thus formed solids are then admixed with molten fat or wax or a mixture thereof and the resulting molten mixture sprayed through an air/liquid spray nozzle equipped with a heated jacket to maintain the incoming air and the molten phase at a temperature above the melting point. The microspheres are formed as the molten droplets cool. These are collected on a series of sieves in the desired size range of about 45 to 180 microns and retained for use. Microspheres which are not of the desired size range are recycled. Alternatively, the homogeneous mixture is fed onto a centrifugal disc and the microspheres thus formed collected as above, or the molten mixture are cooled and milled to the desired average particle size range.

The biologically active microspheres are then dispersed in a pharmaceutically and pharmacologically acceptable liquid vehicle for injection into the animal. The microsphere-liquid composition is generally administered by subcutaneous injection under the skin of the animal usually in the vicinity of the head, neck or ears.

The animal somatotropins of the present invention also are prepared as biocompatible implants which are injected under the skin of the animal using a conventional pellet implant gun. These compositions are prepared by admixing a powdered modified or derivatized somatotropin with a wax such as castor wax or with a mixture of a copoly (glycolide/lactide), magnesium hydroxide, and a condensate of ethylene oxide prepared with a hydrophobic base formed by condensation of propylene oxide with propylene glycol. The thus formed compositions are then introduced into a pelleting press and formed into cylindrical pellets about ⅛ inch in diameter. The thus formed pellets are administered with a conventional pellet implant gun.

Preparation of the recombinant animal somatotropins in a size range suitable for incorporation in microspheres by spray drying is accomplished by dissolving the recombinant animal somatotropin in dilute ammonium hydroxide solution and then adding desired salt solutions such as sodium benzoate. A nonionic surfactant such as a block copolymer of ethylene oxide and propylene oxide is added and allowed to dissolve with constant gentle mixing. The solution is then spray-dried. A Buchi mini spray dryer, model #190 maybe used for this purpose.

A homogeneous mixture of the thus prepared active ingredient and additives in the molten fat, wax or mixture thereof is prepared and the resulting mixture sprayed through an air/liquid spray nozzle equipped with a heated jacket to maintain the incoming air and the molten phase at a temperature above the melting point. The microspheres are formed as the molten droplets cool and are collected on a series of sieves in the desired size range of about 45 to 180 microns and retained for use. Microspheres which are not of the desired size range are collected for recycling. Alternatively, the homogeneous mixture are fed onto a centrifugal disc and the microspheres thus formed are collected as above, or the molten mixtures are cooled and milled to the desired average particle size range.

Waxes and fats which are suitable for use in the compositions of this invention in general have melting points higher than 40° C. *These waxes are defined as a low-melting organic mixture or compound of high molecular weight, solid at room temperature and generally similar in composition to fats and oils except that it contains no glycerides. Some are hydrocarbons; others are esters of fatty acids and alcohols. They are classed among the lipids. Waxes are thermoplastic, but since they are not high polymers, they are not considered in the family of plastics. Common properties are water repellency; smooth texture; nontoxicity; freedom from objectionable odor and color. They are combustible, and have good dielectric properties. Soluble in most organic solvents; insoluble in water. The major types are as follows:

I. Natural
 1. Animal (beeswax, lanolin, shellac wax, Chinese insect wax).
 2. Vegetable (carnauba, candelilla, bayberry, sugar cane)
 3. Mineral
  (a) Fossil or earth waxes (ozocerite, ceresin, montan)
  (b) petroleum waxes (paraffin, microcrystal-line) (slack or scale wax)

II. Synethetic
 1. Ethylenic polymers and polyol ether-esters ("Carbowax," sorbitol)
 2. Chlorinated naphthalenes ("Halowax")
 3. Hydrocarbon type via Ficher-Tropsch synthesis

*The Condensed Chemical Dictionary Tenth Edition Pg. 1094 Van Nostrand Reinhold Publisher The fat may be defined as a glyceryl ester of higher fatty acids such as stearic and palmitic. Such esters and their mixtures are solids at room temperatures and exhibit crystalline structure. Lard and tallow are examples. There is no chemical difference between a fat and an oil, the only distinction being that fats are solid at room temperature and oils are liquid. The term "fat" usually refers to triglycerides specifically, whereas "lipid" is all-inclusive.

The fat is preferably long chain $C_{10}$–$C_{24}$ fatty acid, alcohol, ester, salt, ether or mixture thereof, with mono-, di-, or triglycerides composed predominantly of stearates, palmitates, laurates, linoleates, linolenates, oleates, and residues or mixtures thereof, having melting points greater than 50° C. being most preferred. Glycerol tristearate is a most preferred fat. Additionally, lipophilic salts of fatty acids such as magnesium stearate and the like are also suitable.

The microspheres useful in the invention are dispersed in a pharmaceutically and pharmacologically acceptable liquid to obtain a slow release composition for parenteral administration. The vehicle is aqueous buffered systems or oil systems. The oil is a vegetable or an animal oil. A preferred oil is a neutral triglyceride liquid fat. A neutral oil is one containing no residual acid. Vehicles suitable for use in the compositions of this invention include aqueous systems such as buffered salines; organic solvents such as glycols and alcohols; and water immiscible liquids such as oils, depending upon the solubility of the active ingredient being administered.

Implants are prepared by weighing a sufficient quantity of the ground homogeneous mixture of the desired animal somatotropin and the desired diluents. This mixture is then compressed on a carver press at from 1000 to 5000 psig in a 3/16" or ¼" diameter cylindrical die or on a rotary tablet press using the required punch and die. The implants thus prepared are then coated with either biodegradable or nonbiodegradable coatings as provided herein.

Clean grade silicon elastomer (10 parts) is mixed with curing agent (one part) on a watch glass with a spatula. This is deaerated in a dessicator for 30 minutes. The implants are grasped by the ends with tweezers, rolled into the silicon polymer, placed on end on aluminum foil and cured at 40° C. for five hours. One or both of the ends are removed with a razor blade leaving the "shaft" of the cylinder coated.

Alternatively, implants are dip coated with 20% to 40% of a medical adhesive, sold under the trademark SILASTIC, by Dow Corning, which has been dispersed in hexane, and dried and cured at 40° C. to 50° C. overnight before removing the coating from one or both of the base ends.

Alternatively, the polymer or copolymer (one part) is dissolved in chloroform (three to eight parts). Each implant is grasped by the ends with tweezers, dipped into the polymer solution, and then the chloroform evaporated at room temperature. Each implant is coated twice. After the coating dried overnight at room temperature, the polymer ends are removed with a razor blade, leaving the long cylindrical "shaft" coated.

| | Implant formulation | | |
|---|---|---|---|
| % somatotropin | % Magnesium stearate | % ethyl cellulose | % Castor Wax |
| 50 | — | 5.0 | 45 |
| 40 | — | 5.0 | 50 |
| 20 | — | 5.0 | 75 |
| 50 | 0.5 | 3.5 | 46 |
| 20 | 0.5 | 3.5 | 76 |

| *somatotropin | % cholesterol | % surfactant | % glyceryl tristearate |
|---|---|---|---|
| 30 | 68 | 2 | — |
| 15 | 41.5 | 2 | 41.5 |

| % somatotropin | % stearic acid |
|---|---|
| 50 | 50 |
| 20 | 80 |

Also, the recombinant animal somatotropins is blended with surfactants, buffer salts, and/or preservatives in an aqueous solution. This solution is then spray-dried in a Buchi Model 190 spray dryer giving a small particle size powder. This powder is then melt-blended with a fat or wax and molded into cylindrical implants. The implants prepared are then coated with either a biodegradable or a non-degradable polymer using the various procedures A or B.

| | Implant Formulations | | |
|---|---|---|---|
| % somototropin | % glyceryl tristearate | % sodium benzoate | % surfactant |
| 28 | 69.9 | 2.0 | 0.15 |
| 15 | 82.9 | 2.0 | 0.15 |
| 50 | 48.5 | 1.5 | 0 |

Dose

In Table I, a 10.3 mg dose of a daily injectable bovine somatotropin plus two sustained release doses of bovine somatotropin are reviewed for milk yield and composition. The sustained release doses of 175 mg or 350 mg are injected every fourteen days and treatments beginning about 14 weeks after calving.

TABLE I

| Parameter | 0.0 | 10.3 | 175 | 350 |
|---|---|---|---|---|
| Milk, kg/day | 21.60 | 24.75 | 24.78 | 24.74 |
| 3.5% fat-corrected milk, kg | 23.06 | 26.46 | 26.76 | 25.80 |
| Milk fat, % | 4.12 | 4.21 | 3.98 | 4.02 |
| Milk protein, % | 3.33 | 3.29 | 3.18 | 3.21 |

EXAMPLE 3

BST also increases milk yield in a dose-dependent fashion when administered beginning approximately 4 weeks after calving. The following table reports average daily milk yield for cows administered 10.3 or 20.6 mg BST as a daily injection from 6 University dose-titration experiments. BST herein refers to rBST.

TABLE II

| Parameter | 0.0 | 10.3 | 20.6 |
|---|---|---|---|
| Milk, lbs/day | 60.32 | 68.75 | 72.87 |
| 3.5% fat-corrected milk, lbs | 60.11 | 68.13 | 72.16 |

EXAMPLE 4

Experimental Animals - Resumption of BST

In another experiment, the effect of cessation and resumption of BST injections on concentration of plasmin in milk and milk yield is determined. Four cows at >310 days of lactation with a history of daily BST injection are assessed for daily milk yield and milk plasmin activity. These measurements are taken 3 days prior to cessation of BST injection (end of safety-efficacy trial), for four days after cessation of BST injections and for 3 days following resumption of BST injections. In this study, daily injections contain 10.3 mg of BST in saline and are administered daily between 0930 and 1000 h in the shoulder region.

EXAMPLE 5

Plasmin and Plasminogen Analysis

Plasmin and plasminogen concentrations in milk serum or casein fractions are determined by the method of Koryoka-Dahl et al. with a slight modification. As plasmin has proteolytic sepcificity similar to trypsin, it will cleave amide bonds on the carboxy-terminal side of lysine and arginine residues. Briefly, this method involves assaying for plasmin activity by measuring the rate of hydrolysis of the chromogenic substrate (H-D-valyl-L-leucyl- L-lysine-p-nitroanilide dihydrochloride, S2251). Three amino acids are required to minimize interference from other serine proteases. Formation of p-nitroanilide resulting from substrate cleavage by plasmin is measured spectrophotometrically at 405 nm. A standard curve is prepared to convert plasmin activity to plasmin concentration by plotting change in absorbance versus concentration of plasmin over the range of 0 to 3 mg/l. This conversation is made to overcome the difficulty in comparing plasmin activity units, which are not uniform in the literature. Plasminogen is the inactive form of plasmin. In this assay a plasminogen-activating substance, urokinase, is added to quantitatively convert all of the plasminogen to plasmin. When plasmin activity is again assayed, any increase in activity can be said to be derived from plasminogen. Thus the ratio of plasminogen to plasmin is a useful index in determining the degree of activation of the system.

Least square analysis of variance is performed to examine the effect of exogenous somatotropin administration on milk plasmin and plasminogen concentrations and milk yield. The mathematical model includes lactation number, stage of lactation and treatment as fixed classification effects, the interaction between stage of lactation and treatment, log somatic cell counts (SCC) and milk yield as covariates plus a random residual term. The effect of milk yield is removed from the model when testing the significance of the other factors on milk yield. For data analysis there are five subclasses for lactation number (1, 2, 3, 4, 5). Treatment consisted of two subclasses; control and treated. All BST treated groups are grouped into one category defined as treated. This is possible as there are no statistically significant differences in response among BST treatments. Stage of lactation is classified into 10 subclasses with subclasses 1 to 9 consisting of cows in their first to ninth month of lactation, respectively. The last subclass contains samples from cows with more than 9 months in lactation.

EXAMPLE 6

Plasmin Levels in Milk Production

In FIG. 1, the relationship between milk plasmin and milk yield is presented for control cows and for those treated with exogenous BST (all levels). Increasing plasmin concentration in milk as lactation progresses has been reported previously by Politis et al. (13) and others (10). The present results show that plasmin levels remain depressed throughout lactation in cows injected with BST (FIG. 1). Similarly, the total plasmin produced (milk volume×plasmin concentration) is maintained at low levels in milk from cows injected with BST. In contrast, cows injected with placebo show a gradual increase in the total production and concentration of milk plasmin as lactation advances. The milk yield data have been superimposed to illustrate the inverse relationship between milk plasmin concentration and milk yield. The BST-injected cows have persistently higher milk yields and low milk plasmin concentration and total secretion.

Figure 2:
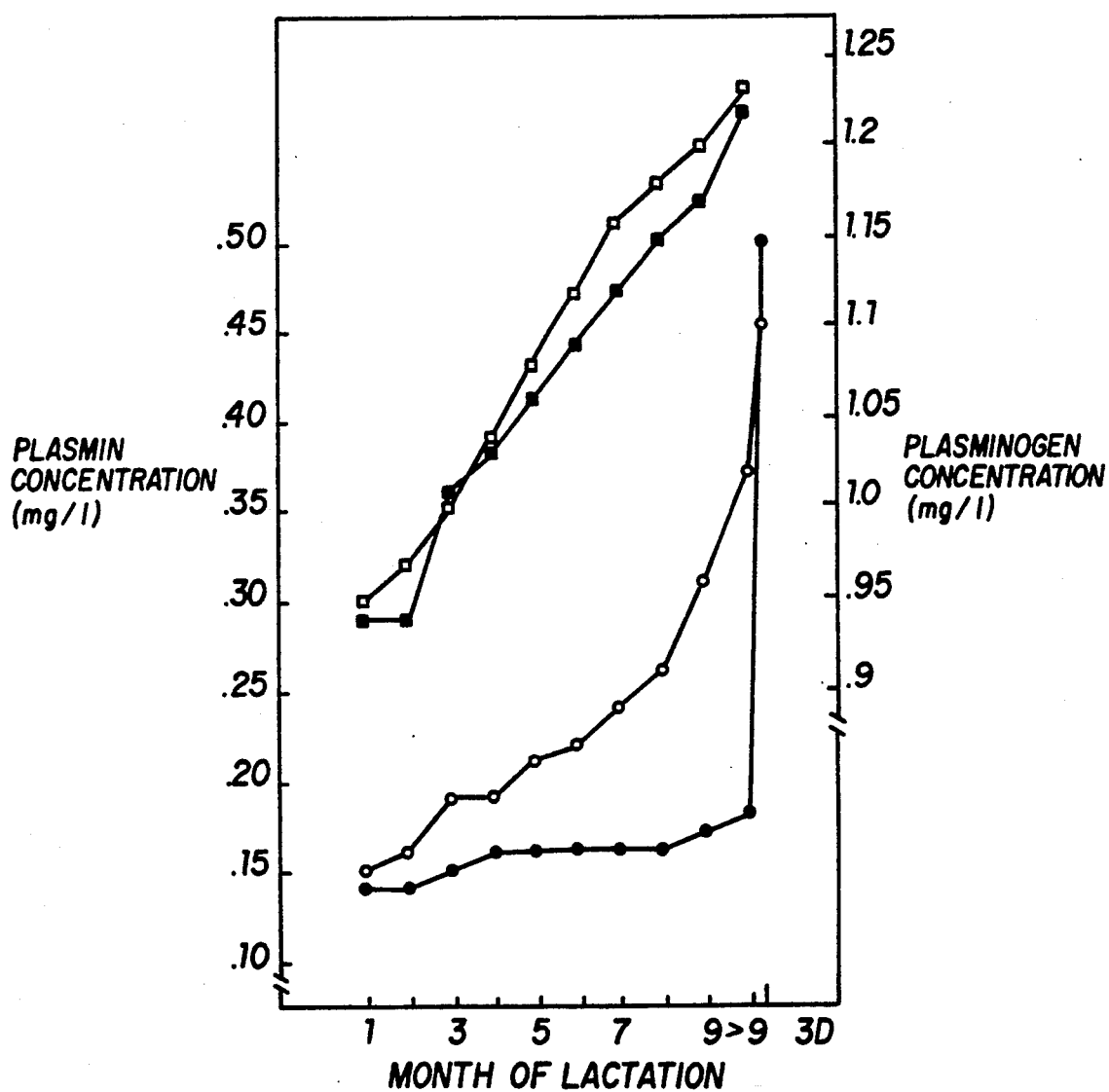
FIG. 2: Effect of rBST-injections on milk plasminogen and plasmin concentration through lactation and 3 days after drying off. Plasmin concentrations are represented for control cows (●) and rBST-injected cows (●). Milk plasminogen concentrations are shown for control cows (□) and rBST-injected cows (■). All values represent least squares means.

Milk plasmin is influenced by the availability of precursor plasminogen and the presence of plasminogen activators and plasminogen activator inhibitors. Plasminogen is not limiting in animals injected with BST as milk plasminogen levels are not significantly different between BST-injected and control cows (FIG. 2). This continues into the dry period where at 3 days after the last milking plasminogen levels were 1.49±.08 and 1.39±.08 mg L$^{-1}$ in secretions from BST-injected and control animals, respectively. The process regulating milk plasminogen is apparently insensitive to BST. The ratio of plasminogen to plasmin is a useful index of plasminogen activation. This measurement is independent of milk volume. In milk from BST-injected cows, this ratio remains remarkably constant throughout lactation. However, 3 days after drying off, this ratio falls dramatically, indicating massive activation of plasminogen and production of plasmin (FIG. 2). In milk from control cows, the plasminogen/plasmin ratio falls from 6.3 in the first month to 3.6 at >9 months of lactation. The activation process is thus gradual throughout the lactation period.

Figure 3A:
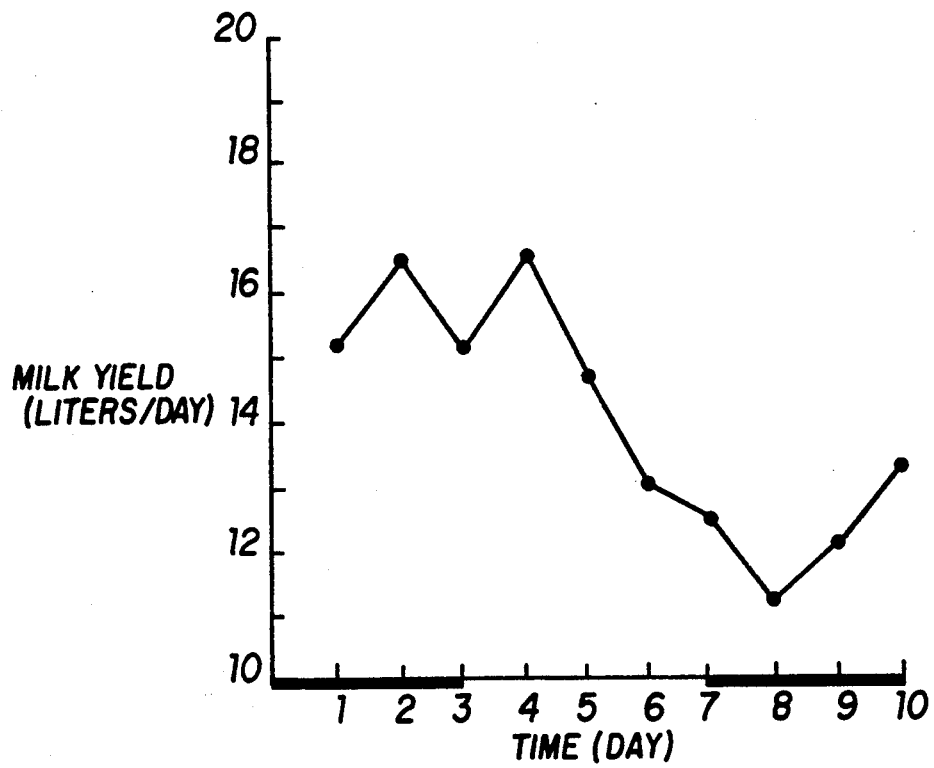
FIG. 3A–3B: Relationship between daily milk yield and milk plasmin concentration (mean, n=4) during cessation and resumption of rBST treatment in late lactation. Dark areas on the X axis indicate daily rBST injections. Light areas on the Y axis indicate cessation of rBST injections.
Figure 3B:
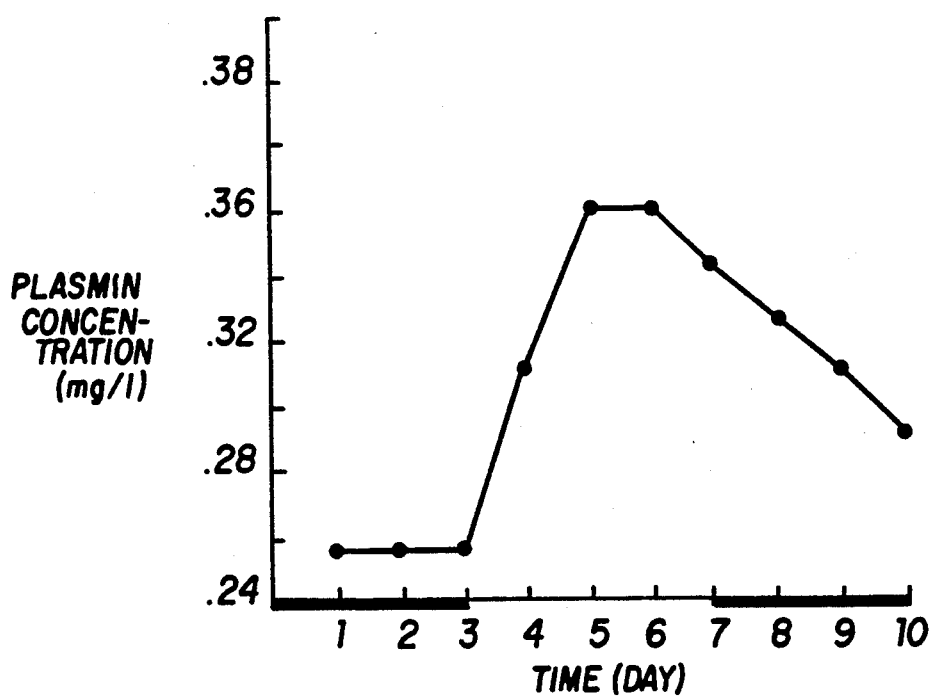

In an effort to gain insight into the time course and reversibility of BST effects on decreased milk plasmin and increased milk yield, BST injections are abruptly ceased as cows conclude the safety-efficacy trial for 4 days then resume injections (FIG. 3). Plasmin concentrations in the milk rises during the first day and reaches the peak at the second day, while milk yield is initially unaffected, then decreases. When BST injections are resumed, plasmin concentrations decrease while milk yield continue to decrease, then increase in a lag fashion (FIG. 3). These data show that alterations in BST lead to prompt changes in milk plasmin levels prior to changes in milk yield.

EXAMPLE 7

Two cows were selected to represent extremes in milk plasmin concentrations; one late lactation, high somatic cells (#628), the other early lactation, low somatic cells (#659). Milk was collected, assayed for plasmin, plasminogen cheese total solids and cheese yield determined. Milk plasmin concentration was three fold higher in cow #628 (Table II). Cheese total solids were higher for cow #659, while milk protein levels appeared lower. Increased cheese total solids would indicate higher quality curds for cheese production, and should indicate greater cheese yield. While cheese yield was not different in this very limited experiment total protein was lower in milk containing lower plasmin. Calculating cheese yield on an equal milk protein basis would result in increased cheese yield from the cow having lower milk plasmin concentration.

TABLE III

Properties of Milk from Cows of Differing Milk Plasmin Concentration

| Parameter | #659[1] | #628[2] |
|---|---|---|
| Plasmin, mg/l milk | .085 | .253 |
| Cheese total solids, % | 55.8 | 50.6 |
| g total solids/100 g milk | 6.3 | 5.9 |
| Milk fat, % | 3.19 | 3.20 |
| Milk protein, % | 3.03 | 3.42 |
| Cheese yield, % | 11.22 | 11.56 |
| Cheese yield/unit milk protein | 3.70 | 3.38 |

[1]Early lactation, low somatic cells
[2]Late lactation, high somatic cells

References

1. Akers, R. M. 1985. Lactogenic hormones: Binding sites, mammary growth, secretory celldifferentiation and milk biosynthesis in ruminants. J. Dairy Sci. 68:501.
2. Baer, R. J., K. M. Treszen, D. J. Schingoethe, D. P. Casper, W. A. Eisenbeisz, R. D. Shaver and R. M. Cleale. 1989. Composition and Flavor of Milk Produced by Cows Injected with Recombinant Bovine Somatotropin. J. Dairy Science. 72:in press.

3. Bauman, D. E., P. J. Eppard, M. J. DeGeeter and G. M. Lanza. 1985. Responses of high-producing dairy cows to long term treatment with pituitary somatotropin and recombinant somatotropin. J. Dairy Sci. 68:1352.

4. Collier, R. J., R. Li, H. D. Johnson, B. A. Becker, F. C. Buonomo and K. J. Spencer. 1988. Effect of sometribove on plasma insulin-like growth factor I and II in cattle exposed to heat and cold stress. J. Dairy Sci. 71 (Suppl. 1):228.

5. Cotes, P. M., J. A. Crichton, S. J. Folley and F. G. Young. 1949. Galactopioetic activity of purified anterior pituitary growth hormone. Nature 164:992.

6. DeJong, L. 1976. Protein breakdown in soft cheese and its relation to consistency. Neth. Milk Dairy J. 30:242.

7. Disenhaus, C., L. Belair and J. Djane. 1988. Caracterisation et evolution physiologique des recepteurs pour les insulin-like growth factor I and II dans la glande mammaire de brebis. Reprod. Nutr. Develop. 28:241.

8. Donnelly, W. J. and J. Gerard Barry. 1983. Casein compositional studies. III. Changes in Irish milk for manufacturing and role of milk protease. J. Dairy Res. 50:433–441.

9. Elvinger, F., H. H. Head, C. J. Wilcox, R. P. Natzke, R. G. Eggert. 1988. Effects of administration of bovine somatotropin on milk yield and composition. J. Dairy Sci. 71:1515–1525.

10. Eppard, P. J., D. E. Bauman, J. Bitman, D. L. Wood, R. M. Akers, W. A. House. 1985. Effect of dose bovine growth hormone on milk composition: a Lactalbumin, fatty acids and mineral elements J. Dairy Sci. 68:3047–3054.

11. Gertler, A., N. Cohen and A. Macz. 1983. Human growth hormone but not ovine or bovine growth hormones exhibit galactopoietic prolactin-like activity in organ culture from bovine lactating mammary gland. Mol. Cell. Endocr. 33:162.

12. Hart, I. C., J. A. Bines, S. V. Morant and J. L. Ridley. 1978. Endocrine control of energy metabolism in the cow: Comparison of the levels of hormones (prolactin, growth hormone, insulin and thyroxine) and metabolites in the plasma of high- and low-yielding cattle at various stages of lactation. J. Endocr. 77:333.

13. Hart, I. C., J. A. Bines and S. V. Morant. 1980. The secretion and metabolic clearance rates of growth hormone, insulin and prolactin in high- and low-yielding cattle at four stages of lactation. Life Sciences 27:1839.

14. Holst, B. D., W. L. Hurley and D. R. Nelson. 1987. Involution of the bovine mammary gland. Histology and ultrastructural changes. J. Dairy Sci. 70:935.

15. Koryoka-Dahl, M., B. Ribadeau-Dumas, N. Chene and J. Marta. 1983. Plasmin activity in milk. J. Dairy Sci. 66:704.

16. Larsson, L. -T., L. Skriver, L. S. Nielsen, J. Grondahl-Hansen, P. Kristensen and K. Dano. 1984. Distribution of urokinase-type plasminogen activator immunoreactivity in the mouse. J. Cell. Biol. 98:894.

17. Ossowski, L., D. Biegel and E. Reich. 1979. Mammary plasminogen activator: Correlation with involution, hormonal modulation and comparison between normal and neoplastic tissue. Cell 16:929.

18. Pearse, M. J., P. M. Linklater, R. J. Hall, A. G. MacKinlay. 1986. Extensive degredation of casein by plasmin does not impede subsequent curd formation and syneresis. J. Dairy Res. 53:477–480.

19. Politis, I., E. Lachance, E. Block and J. D. Turner. 1988. Plasmin/plasminogen in bovine milk: A relationship with involution. J. Dairy Sci. 72:900.

20. Richard, A. L., S. N. McCutcheon and D. E. Bauman. 1985. Responses of dairy cows to exogenous bovine growth hormone administered during early lactation. J. Dairy Sci. 68:2385. 21.

21. Richardson, B. C. 1983. Variation of the concentration of plasmin and plasminogen in bovine milk with lactation. NZ J. Dairy Sci. and Tech. 18:247–252.

22. Soderholm, C. G., D. E. Otterby, J. G. Linn, F. R. Ehle, J. E. Wheaton, W. P. Hansen and R. J. Annexstad. 1988. Effects of recombinant bovine somatotropin on milk production, body composition and physiological parameters. J. Dairy Sci. 71:355–365.

23. Turner, J. D., P. Rotwein, J. Novakofski and P. J. Bechtel. 1988. Induction of messenger RNA enceding insulin-like growth factors I and II during growth hormone stimulated skeletal muscle hypertrophy. Am. J. Physiol. 255:E 513.

24. Walstra, P. and R. Jenness. Dairy Chemistry and Physics. 1989 by John Weley and Sons, N.Y., pp. 132.

What is claimed is:

1. In a method for making cheese, the improvement comprising: administering to a milk-producing animal, a plasmin-affecting amount of exogenous animal somatotropin, wherein said plasmin level in said milk used to produce cheese is maintained at less than 0.2 mg/l.

2. A method according to claim 1, wherein said exogenous animal somatotropin is bovine somatotropin, caprine somatotropin or ovine somatotropin.

3. A method according to claim 2, wherein said milk-producing animal is a cow, goat, buffalo or sheep.

4. A method according to claim 3, wherein said somatotropin is administered daily or in a sustained release formulation.

* * * * *